(12) United States Patent
Batie et al.

(10) Patent No.: US 7,914,993 B2
(45) Date of Patent: *Mar. 29, 2011

(54) PROCESS FOR STARCH LIQUEFACTION AND FERMENTATION

(75) Inventors: Christopher J. Batie, Durham, NC (US); Greg Crabb, Wake Forest, NC (US); George W. Aux, Durham, NC (US); Edward S. Cates, Raleigh, NC (US); Jay Austin Dinwiddie, Morrisville, NC (US); Aron Louis Silverstone, Durham, NC (US); Rene Quadt, Chapel Hill, NC (US); Carl A. Miller, Raleigh, NC (US)

(73) Assignee: Syngenta Participations AG., Basel (CH)

( * ) Notice: Subject to any disclaimer, the term of this patent is extended or adjusted under 35 U.S.C. 154(b) by 356 days.

This patent is subject to a terminal disclaimer.

(21) Appl. No.: 12/128,718

(22) Filed: May 29, 2008

(65) Prior Publication Data

US 2008/0299256 A1 Dec. 4, 2008

Related U.S. Application Data

(60) Provisional application No. 60/932,751, filed on Jun. 1, 2007.

(51) Int. Cl.
*C12Q 1/68* (2006.01)
(52) U.S. Cl. ............................................ 435/6; 435/202
(58) Field of Classification Search .................. 800/284, 800/278, 287, 288; 435/161, 202, 468, 69.8, 435/99, 6
See application file for complete search history.

(56) References Cited

U.S. PATENT DOCUMENTS

| | | | |
|---|---|---|---|
| 5,366,883 A | 11/1994 | Asada | |
| 5,543,576 A | 8/1996 | Van Ooijen et al. | |
| 5,705,375 A | 1/1998 | Van Ooyen et al. | |
| 6,147,277 A | 11/2000 | Gausing et al. | |
| 6,737,563 B2 | 5/2004 | Yu et al. | |
| 7,102,057 B2 * | 9/2006 | Lanahan et al. | 800/284 |
| 7,407,677 B2 | 8/2008 | Callen et al. | |
| 7,727,726 B2 * | 6/2010 | Cates et al. | 435/6 |
| 2004/0018607 A1 | 1/2004 | Callen et al. | |
| 2004/0063184 A1 | 4/2004 | Grichko | |
| 2004/0234649 A1 | 11/2004 | Lewis | |
| 2005/0054071 A1 | 3/2005 | Udagawa | |
| 2006/0026715 A1 | 2/2006 | Hood | |
| 2006/0230473 A1 | 10/2006 | Johnson | |
| 2007/0037267 A1 | 2/2007 | Lewis | |
| 2007/0134780 A1 | 6/2007 | Grichko | |
| 2007/0178567 A1 | 8/2007 | Lewis | |
| 2007/0190620 A1 | 8/2007 | Mueller | |
| 2007/0202214 A1 | 8/2007 | Lewis | |
| 2007/0202583 A1 | 8/2007 | Smith | |
| 2008/0045702 A1 | 2/2008 | Lanahan | |

FOREIGN PATENT DOCUMENTS

| | | |
|---|---|---|
| EP | 0449376 | 2/1991 |
| EP | 0479359 | 8/1992 |
| FR | 2778412 | 11/1999 |
| WO | 9201042 | 1/1992 |
| WO | 92/05259 | 4/1992 |
| WO | 9514099 | 5/1995 |
| WO | 97/32986 | 9/1997 |
| WO | 98/39461 | 9/1998 |
| WO | 03/018766 | 3/2003 |
| WO | 2004/091544 | 10/2004 |

OTHER PUBLICATIONS

GenBank Accession No. AF068255 [online], [retrieved on Sep. 23, 2004]. Retrieved from the Internet: <URL: http://www.ncbi.nlm.nih.gov>.
Jørgensen et al, Cloning, Sequencing, Characterization, and Expression of an Extracellular α-Amylase from the Hyperthermophilic Archaeon Pyrococcus furiosus in *Escherichia coli* and *Bacillus subtilis* The Journal of Biological Chemistry, vol. 272, No. 26, (Jun. 27, 1997) pp. 16335-16342.
Lévêque et al, Cloning and expression of an α-amylase encoding gene from the hyperthermophilic archaebacterium *Thermococcus hydrothermalis* and biochemical characterization of the recombinant enzyme Federation of European Microbiological Societies, vol. 186 (2000), pp. 67-71.
Swiss-Prot Accession No. O08452 [online], [retrieved on Sep. 23, 2004]. Retrieved from the Internet: <URL: http://au.expasy.org>.
Swiss-Prot Accession No. O33476 [online], [retrieved on Sep. 23, 2004]. Retrieved from the Internet: <URL: http://au.expasy.org>.
Tachibana et al, Cloning and Expression of the α-Amylase Gene from the Hyperthermophilic Archaeon *Pyrococcus* sp. KOD1, and Characterization of the Enzyme Journal of Fermentation and Bioengineering, vol. 82, No. 3 (1996) pp. 224-232.
Taylor et al, Fermentation and Costs of Fuel Ethanol from Corn with Quick-Germ Process Applied Biochemistry and Biotechnology, vol. 94 (1) (Apr. 2001), pp. 41-50.
GenBank Accession No. AF504064 [online], [retrieved on Feb. 15, 2006]. Retrieved from the Internet: <URL: http://www.ncbi.nlm.nih.gov>.

(Continued)

*Primary Examiner* — Tekchand Saidha
(74) *Attorney, Agent, or Firm* — Syngenta Biotechnology Inc.

(57) ABSTRACT

The presently disclosed subject matter provides improved processes for processing starch from plant sources, including processes for starch liquefaction, for simultaneous liquefaction and saccharification, and for the preparation of ethanol. These processes can be performed without a pH adjustment and at relatively low temperatures. The processes can involve the use of starch-containing plant material derived from plants that express starch-digesting enzymes. The presently disclosed subject matter further relates to improved processes for the preparation of other starch-derived products, including dried distiller grain (dried distiller grain) and dried distiller grain and solubles (dried distiller grain and solubles), and to the starch-derived products, themselves.

33 Claims, 2 Drawing Sheets

OTHER PUBLICATIONS

GenBank Accession No. AY608688 [online], [retrieved on Feb. 15, 2006]. Retrieved from the Internet <URL: http://www.ncbi.nlm.nih.gov>.

GenBank Accession No. AF017454 [online], [retrieved on Feb. 15, 2006]. Retrieved from the Internet <URL: http://www.ncbi.nlm.nih.gov>.

GenBank Accession No. D83793 [online], [retrieved on Feb. 15, 2006]. Retrieved from the Internet <URL: http://www.ncbi.nlm.nih.gov>.

GenBank Accession No. AF504063 [online], [retrieved on Feb. 15, 2006]. Retrieved from the Internet <URL: http://www.ncbi.nlm.nih.gov>.

GenBank Accession No. AF504062 [online], [retrieved on Feb. 15, 2006]. Retrieved from the Internet <URL: http://www.ncbi.nlm.nih.gov>.

Rogers et al., Isolation and Sequence Analysis of a Barley Alpha-Amylase cDNA Clone, The Journal of Biological Chemistry. Jul. 1983, vol. 258, No. 13, pp. 8169-8174.

Syngenta Participations AG, International Publication No. WO2003/018766, International Search Report, (Mar. 6, 2003).

Syngenta Participations AG, International Publication No. WO2005/096804, International Search Report, (Oct. 20, 2005).

Pen, et al., Production of Active Bacillus Licheniformis Alpha-Amylase in Tobacco and its Application Bio/Technology, vol. 10(3) (Mar. 1992) pp. 292-296.

Murray, et al., Codon usage in plant genes Nucleic Acids Research, vol. 17 (1989) pp. 477-498.

European Patent Application Ser. No. 04718580.6, Syngenta Participations AG, "International Search Report" dated Apr. 1, 2008.

Wada, et al., Codon usage tabulated from the GenBank genetic sequence data Nucleic Acids Research, vol. 18 Supplement (1990) pp. 2367-2411.

GenBank Accession No. AF504065 [online], [retrieved on Feb. 15, 2006]. Retrieved from the Internet <URL: http://www.ncbi.nlm.nih.gov>.

Atschul et al., Basic Local Alignment Search Tool Journal of Molecular Biology, vol. 215 (1990) pp. 403-410.

Syngenta Participations AG, International Application Ser. No. PCT/US08/65105 "International Search Report", Oct. 17, 2008.

Wolt et al., "Estimated Environmental Loads of Alpha-amylase from Transgenic High-amylase Maize", Biomass and Bioenergy, vol. 31, No. 11-12 (May 25, 2007).

Korba, "Enticed to Surpass Nameplate", Ethanol Producer Magazine, (Sep. 2006).

* cited by examiner

PROCESS FOR STARCH LIQUEFACTION AND FERMENTATION

FIELD OF INVENTION

The presently disclosed subject matter pertains to processing starch from plant sources.

BACKGROUND OF THE INVENTION

Plants are often used as a source for starch, which can be used to produce ethanol and other products. Plant starches are generally in a granular form, which is insoluble in water. Starch is initially collected from plant grains using either a wet milling, a dry milling or a dry grind process.

To produce ethanol, starch containing fractions derived from wet milling or ground grain from dry grinding are further hydrolyzed into fermentable sugars which are then fermented to make ethanol. Several plant starch processing methods exist including a raw starch process, which involves little to no heating of the milled plant material being processed; or higher temperature hydrolysis of starch frequently referred to as "liquefaction". In either of these methods for breaking down starch derived from plants, the conventional process involves the addition of enzymes, frequently liquid enzymes, to the milled plant starch in a slurry tank.

Liquefaction methods often involve a starch gelatinization process, wherein aqueous starch slurry is heated so that the granular starch in the slurry swells and bursts, dispersing starch molecules into the solution. During the gelatinization process, there is a dramatic increase in viscosity. To enable handling during the remaining process steps, the starch must be thinned or "liquefied". This reduction in viscosity can be accomplished by enzymatic degradation in a process referred to as liquefaction. During liquefaction, the long-chained starch molecules are degraded into smaller branched and linear chains of glucose units (dextrins) by an enzyme, such as alpha-amylase (i.e., α-amylase).

A conventional enzymatic liquefaction process comprises a three-step hot slurry process. The slurry is heated to between 80-85 degrees C. to initiate gelatinization and α-amylase is added to initiate liquefaction. The slurry is jet-cooked at temperatures between 105 and 125 degrees C. to complete gelatinization of the slurry, cooled to 60-95 degrees C. (e.g., between 90-95 degrees C.), and, usually, additional α-amylase is added to finalize hydrolysis during a secondary liquefaction step. This three step process is employed in order to break down as much of the plant starch as possible. A process that avoids the use of a jet cooker or a secondary liquefaction would be advantageous to ethanol production as this would save considerable time, effort, and costs associated with heating, cooling and transferring the slurry between tanks.

Liquefaction results in the generation of dextrins as the starch is hydrolyzed. The dextrins can be broken down further during saccharification, to produce low molecular weight sugars that can be metabolized by yeast. The saccharification hydrolysis is typically accomplished using glucoamylases and/or other enzymes such as α-glucosidases and/or acid α-amylases. A full saccharification step typically lasts up to 72 hours. However, it is also common to perform only a pre-saccharification step of about 40 to 90 minutes at a temperature above 50 degrees C., followed by a complete saccharification during fermentation in a process known as simultaneous saccharification and fermentation (SSF).

Prior to entering the fermentation tank, the slurry must be cooled to about ambient temperature. The slurry is typically pumped through a heat exchanger to cool the slurry. It is important that the slurry remain in a relatively fluid form during this process. As the slurry thickens due to cooling, it places added pressure on the heat exchanger. A process improvement that avoids excessive thickening of the post liquefaction slurry when cooled to ambient temperature is an advantage to the ethanol producer.

Fermentation can be performed using yeast, e.g., a *Saccharomyces* spp. Typical SSF times range from 40 to 60 hours. After SSF, ethanol is recovered by distillation. The residual solids and liquids can be dried to make the fermentation co-product dried distillers grains (DDG) and dried distillers grains and solubles (DDGS). A portion of the liquid streams from the distillation (referred to as backset or stillage) can be recycled back to the process.

The natural pH of milled corn grain is approximately pH 5.8 to approximately pH 6.0; however when combined with recycled process water (backset) in the slurry tank, the pH is approximately pH 4.8 at 30 to 33% dry solids. The pH is typically adjusted to approximately 5.8 before the liquefaction step in order to be compatible with the biochemical properties of commercial thermostable amylases. An large dosage of the enzyme would be required at pH 4.8. After the jet cooking and secondary liquefaction, the pH must be decreased to pH 4.8 for simultaneous saccharification and fermentation (SSF), saccharification and subsequent fermentation, or fermentation without saccharification.

Given the increasing importance of ethanol as a fuel, improvement to the process is desirable.

SUMMARY OF THE INVENTION

The presently disclosed subject matter provides a method of increasing the percentage of solids in a slurry while maintaining a desired viscosity of the slurry as it progresses through the ethanol production process. A method for reducing the viscosity of a slurry is also described. A method for reducing the formation of dough balls in a slurry is also provided. The slurry comprises an admix of transgenic plant material expressing at least one starch-digesting enzyme.

DETAILED DESCRIPTION OF THE INVENTION

Figure 1A:
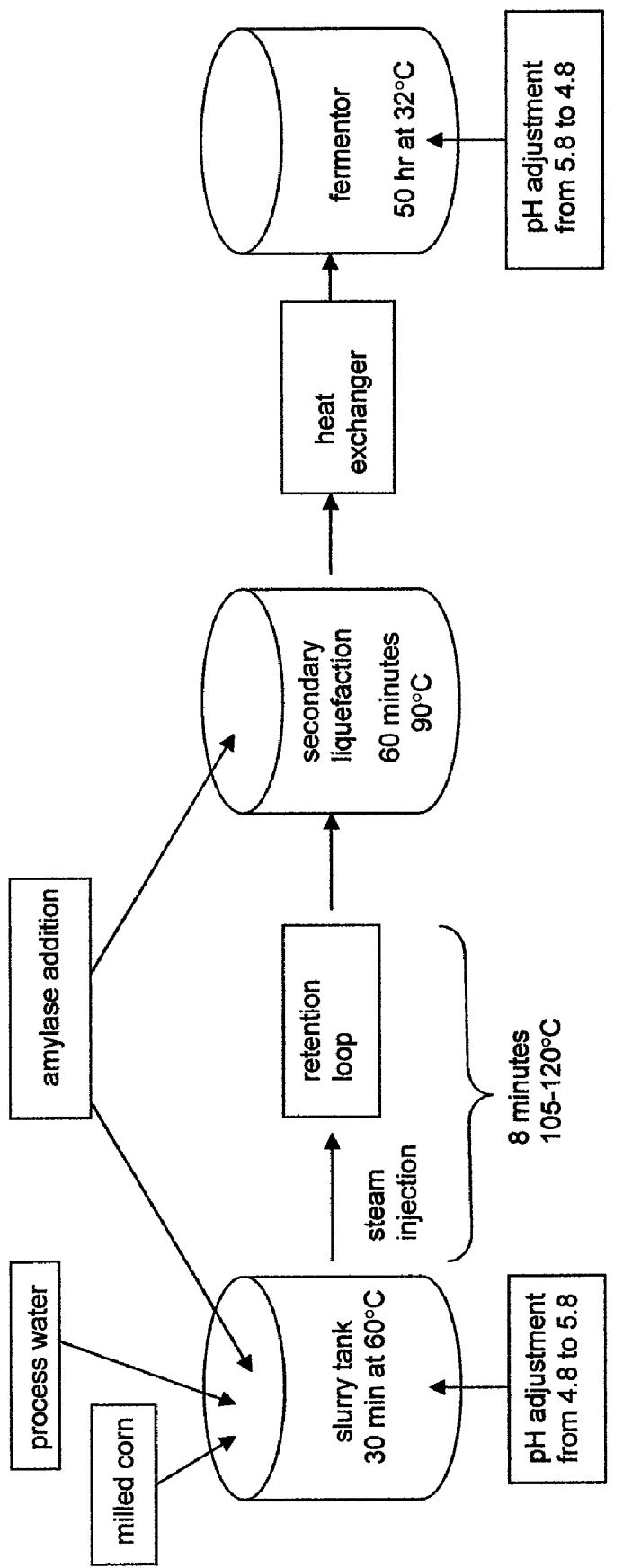
FIG. 1A is a schematic drawing showing a typical conventional dry grind process for preparing ethanol from milled corn.

The presently disclosed subject matter will now be described more fully hereinafter with reference to the accompanying Examples, in which representative embodiments are shown. The presently disclosed subject matter can, however, be embodied in different forms and should not be construed as limited to the embodiments set forth herein. Rather, these embodiments are provided so that this disclosure will be thorough and complete, and will fully convey the scope of the embodiments to those skilled in the art.

Unless otherwise defined, all technical and scientific terms used herein have the same meaning as commonly understood by one of ordinary skill in the art to which this presently described subject matter belongs. All publications, patent applications, patents, and other references mentioned herein are incorporated by reference in their entirety.

I. Definitions

Following long-standing patent law convention, the terms "a" and "an" mean "one or more" when used in this application, including the claims. Thus, "an enzyme" or "a plant material" can refer to a plurality (i.e., two or more) enzymes or plant materials.

As used herein, the term "about" modifying any amount can refer to the variation in that amount encountered in real world conditions of producing sugars and ethanol, e.g., in the lab, pilot plant, or production facility. Unless otherwise indicated, all numbers expressing quantities of percentage, weight, temperature, flow rate, time, pH, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

Plant material can be derived from a transgenic plant. As used herein the term "transgenic" refers to plants that include a heterologous polynucleotide. A heterologous polynucleotide can be a polynucleotide isolated from one species of a plant and then transferred back into the same species of plant or a different species. The term "transgenic plant" can refer either to the initially transformed plant or to the progeny of the initially transformed plant. Techniques for transforming plants, plant cells or plant tissues can include, but are not limited to, transformation with DNA employing *A. tumefaciens* or *A. rhizogenes* as the transforming agent, electroporation, DNA injection, microprojectile bombardment, and particle acceleration. See, for example, EP 295959 and EP 138341.

The term "starch-digesting enzyme" includes any enzyme that can catalyze the transformation of a starch molecule or a degradation product of a starch molecule. For example, starch-digesting enzymes include starch-degrading or isomerizing enzymes including, for example, α-amylase (EC 3.2.1.1), endo or exo-1,4- or 1,6-α-D-glucoamylase, glucose isomerase, β-amylases (EC 3.2.1.2), α-glucosidases (EC 3.2.1.20), and other exo-amylases; starch debranching enzymes, such as isoamylase (EC 3.2.1.68), pullulanase (EC 3.2.1.41), neo-pullulanase, iso-pullulanase, amylopullulanase and the like; glycosyl transferases such as cyclodextrin glycosyltransferase and the like. Starch-digesting enzymes can be used in conjunction with other enzymes that can facilitate the release of starch from plant tissue. Starch-digesting enzymes can be used in conjunction with cellulases such as exo-1,4-β-cellobiohydrolase (EC 3.2.1.91), exo-1,3-β-D-glucanase (EC 3.2.1.39), hemicellulase, β-glucosidase and the like; endoglucanases such as endo-1,3-β-glucanase (EC 3.2.1.6) and endo-1,4-β-glucanase (EC 3.2.1.4) and the like; L-arabinases, such as endo-1,5-α-L-arabinase (EC EC 3.2.1.99), α-arabinosidases (EC 3.2.1.55) and the like; galactanases such as endo-1,4-β-D-galactanase (EC 3.2.1.89), endo-1,3-β-D-galactanase (EC 3.2.1.90), 1-galactosidase, α-galactosidase and the like; mannanases, such as endo-1,4-β-D-mannanase (EC 3.2.1.78), β-mannosidase (EC 3.2.1.25), α-mannosidase (EC 3.2.1.24) and the like; xylanases, such as endo-1,4-1-xylanase (EC 3.2.1.8), β-D-xylosidase (EC 3.2.1.37), 1,3-β-D-xylanase, and the like; pectinases and phytases. In some embodiments, the starch-digesting enzyme is α-amylase, pullulanase, α-glucosidase, glucoamylase, amylopullulanase, glucose isomerase, or combinations thereof.

The starch-digesting enzyme can be specifically selected based on the desired starch-derived end product, the end product having various chain lengths based on, e.g., a function of the extent of processing or with various branching patterns desired. For example, an α-amylase, glucoamylase, or amylopullulanase can be used under short incubation times to produce dextrin products and under longer incubation times to produce shorter chain products or sugars. A pullulanase can be used to specifically hydrolyze branch points in the starch yielding a high-amylose starch, or a neopullulanase can be used to produce starch with stretches of α-1,4 linkages with interspersed α-1,6 linkages. Glucosidases can be used to produce limit dextrins, or a combination of different enzymes can be used to make other starch derivatives. In some embodiments, a glucose-isomerase can be selected to convert the glucose (hexose) into fructose.

In particular, α-amylase refers to an enzyme which cleaves or hydrolyzes internal α (1-4) glycosidic bonds in starch to produce α 1-2 bonds and resulting in smaller molecular weight maltodextrins. These smaller molecular weight maltodextrins include, but are not limited to, maltose, which is a disaccharide (i.e., a dextrin with a degree of polymerization of 2 or a DP2), maltotriose (a DP3), maltotetrose (a DP4), and other oligosaccharides. The enzyme α-amylase (EC 3.2.1.1) can also be referred to as 1,4-α-D-glucan glucanohydrolase or glycogenase. A variety of α-amylases are known in the art and are commercially available. An α-amylase can be from a fungal or bacterial origin and can be expressed in transgenic plants. The α-amylase can be thermostable.

Glucoamylase (also known as amyloglucosidase) refers to the enzyme that has the systematic name 1,4-α-D-glucan glucohydrolase (E.C. 3.2.1.3). Glucoamylase removes successive glucose units from the non-reducing ends of starch. A variety of glucoamylases are known in the art and are commercially available. For example, certain glucoamylases can hydrolyze both the linear and branched glucosidic linkages of starch, amylose, and amylopectin. Glucoamylase can be from a fungal origin and can be expressed in transgenic plants. The glucoamylase can be thermostable.

As used herein the term "dextrose equivalents" or "dextrose equivalent" refers to the industry standard for measuring the concentration of total reducing sugars, calculated as glucose on a dry weight basis. Unhydrolyzed granular starch has a dextrose equivalent of virtually zero, whereas the dextrose equivalent of glucose is defined as 100.

The term "slurry" refers to a mixture of starch or a starch-containing material (e.g., milled corn) and an aqueous component, which can include, for example, water, de-ionized water, or a process water (i.e., backset, steam, condensate), or any combination thereof. The terms slurry and mash can be used interchangeably.

The term "admix" or "admixture" refers to a combination of elements. For example, an admix of plant material can refer to mixing 2 or more plant materials together to form a mixture. It is possible to further define the admixture by indicating the percentage of one or more of the elements. The plant material can be comprised of both transgenic and non-transgenic plant material. Transgenic plant material can contain a heterologous transgene encoding an enzyme, an insect control gene, an herbicide tolerance gene, a phytase, a nematode control gene or any other transgenic gene. The transgenic material may be expressing more than one transgene.

As used herein the terms "liquefaction," "liquefy," "liquefact," and variations thereof refer to the process or product of converting starch to soluble dextrinized substrates (e.g., smaller polysaccharides). Liquefact can also be referred to as "mash."

The term "secondary liquefaction" refers to a liquefaction process that takes place after an initial period of liquefaction or after a jet cooking step of a multi-stage liquefaction process. The secondary liquefaction can involve a different temperature than a previous liquefaction step or can involve the addition of additional starch-digesting enzymes (e.g., α-amylase).

As used herein, the terms "saccharification" and "saccharifying" refer to the process of converting polysaccharides to dextrose monomers using enzymes. Saccharification can specifically refer to the conversion of polysaccharides in a liquefact. Saccharification products are, for example, glucose and other small (low molecular weight) oligosaccharides such as disaccharides (a DP2) and trisaccharides (a DP3).

"Fermentation" or "fermenting" refer to the process of transforming sugars from reduced plant material to produce alcohols (e.g., ethanol, methanol, butanol, propanol); organic acids (e.g., citric acid, acetic acid, itaconic acid, lactic acid, gluconic acid, propionate); ketones (e.g., acetone), amino acids (e.g., glutamic acid); gases (e.g., $H_2$ and $CO_2$), antibiotics (e.g., penicillin and tetracycline); enzymes; vitamins (e.g., riboflavin, $B_{12}$, beta-carotene); and/or hormones. Fermentation can include fermentations used in the consumable alcohol industry (e.g., beer and wine), dairy industry (e.g., fermented dairy products), leather industry, and tobacco industry. Thus, fermentation includes alcohol fermentation. Fermentation also includes anaerobic fermentations.

Fermenting can be accomplished by any organism suitable for use in a desired fermentation step. Suitable fermenting organisms are those that can convert DP1-3 sugars, especially glucose and maltose directly or indirectly to the desired fermentation product (e.g., ethanol, propanol, butanol or organic acid). Fermenting can be effected by a microorganism, such as fungal organisms (e.g., yeast or filamentous fungi). The yeast can include strains from a *Pichia* or *Saccharomyces* species. The yeast can be *Saccharomyces cerevisiae*. Bacterial can also be used in a fermentation process. Bacteria include but are not limited to species from *Acetobacter*, engineered *E. coli*, *Clostridium*, *Acidofilous* or *Lactobacter*.

Fermenting can include contacting a mixture including sugars from the reduced plant material with yeast under conditions suitable for growth of the yeast and production of ethanol. In some embodiments, fermenting involves simultaneous saccharification and fermentation (SSF). The amount of yeast employed can be selected to effectively produce a desired amount of ethanol in a suitable time.

"Slurry tank" refers to any tank used to contain ground plant material combined with a liquid. A commercial slurry tank is a slurry tank used in a commercial production setting which may be a dry grind ethanol plant, a grain milling plant using a wet or dry milling process to mill corn grain or may be a food production plant that is combining ground plant flour with liquids in order to form a dough. A commercial slurry tank can be in an ethanol production facility that produces 10 million gallons of ethanol per year, 20 million gallons of ethanol per year, 30 million gallons of ethanol per year, 40 million gallons of ethanol per year, 50 million gallons of ethanol per year, 60 million gallons of ethanol per year, 70 million gallons of ethanol per year, 80 million gallons of ethanol per year, 90 million gallons of ethanol per year or 100 million gallons of ethanol per year, 150 million gallons of ethanol per year, 200 million gallons of ethanol per year, 250 million gallons of ethanol per year or more.

The term "hydrolysis" is defined as a chemical reaction or process in which a chemical compound is broken down by reaction with water. The starch digesting enzymes hydrolyze starch into smaller units as previously described.

II. Milling of Starch Containing Plant Material

A variety of starch containing plant material can be used in the invention. As used herein, the phrase "plant material" refers to all or part of any plant material that includes starch. The plant material can be a grain, fruit, seed, stalk, wood, vegetable, or root. The plant material can be obtained from any plant including but not limited to sorghum (milo), oats, barley, wheat, berry, grape, rye, maize (corn), rice, potato, sugar beet, sugarcane, pineapple, yams, plantain, banana, grasses or trees. Suitable plant material includes grains such as maize (corn, e.g., whole ground corn), sorghum (milo), barley, wheat, rye, rice, and millet; and starchy root crops, tubers, or roots such as potato, sweet potato, and cassava. The plant material can also be obtained as a previously treated plant product such as soy cake generated during the processing of soybeans. The plant material can be a mixture of such materials and by-products of such materials, e.g., corn fiber, corn cobs, stover, or other cellulose- and hemicellulose-containing materials, such as wood or plant residues. Suitable plant materials include corn, either standard corn or waxy corn.

Plant material can be processed by a variety of milling methods including but not limited to wet milling, dry milling, dry grinding, cracking, coarse grinding, fine grinding, fractionating, mixing, flaking, steam flaking, rolling or chopping. The corn wet milling process separates corn into its four basic components: starch, germ, fiber and protein. There are five basic steps to accomplish this process. First the incoming corn is inspected and cleaned. Then it is steeped for approximately 30 to 40 hours to begin hydrolyzing the starch and breaking the protein bonds. The next step in the process involves a coarse grind to separate the germ from the rest of the kernel. The remaining slurry consisting of fiber, starch and protein is finely ground and screened to separate the fiber from the starch and protein. The starch is separated from the remaining slurry in hydrocyclones. The starch then can be converted to syrup or it can be made into several other products through a fermentation process.

In dry milling, the corn is combined with water in a brief tempering process prior to grinding the corn to a flour. The ground corn flour is then fractionated into bran, germ and grits (starchy fractions). The starchy fractions from the dry milling process are used in the production of snack foods and other products including industrial products. The starchy fractions obtained from the dry milling process are typically not used in the production of ethanol.

In dry grinding, the entire corn kernel or other starchy grain is first ground into flour, which is referred to in the industry as "meal" and processed without separating out the various component parts of the grain. The meal is slurried with water or backset to form a "mash". Enzymes are added to the mash to convert the starch to dextrose, a simple sugar. Ammonia is added for pH control and as a nutrient to the yeast. Dry grind ethanol plants require lower capital and production investments than wet-mills.

It is envisioned that embodiments of the invention can be used in conjunction with milling technique (wet milling, dry milling, dry grinding, cracking, coarse grinding, fine grinding, fractionating, mixing, flaking, steam flaking, rolling or chopping). Embodiments of the invention comprising a method of liquefaction can be incorporated into a wet milling, dry milling or dry grinding process.

III. Slurry Tank.

Starch-digesting enzymes can be added to the starch hydrolysis process as either liquid enzyme added when the milled plant material is mixed with water or can be delivered by using transgenic grain expressing the starch-digesting enzyme as described in US patent application US2003/0135885 herein incorporated by reference in its entirety. A complication of combining liquid starch-digesting enzyme with the milled plant material in the slurry tank is the formation of dough balls or starch balls.

Dough balls consist of milled plant material surrounded by a layer of partially hydrolyzed starch. The partially hydrolyzed starch layer prevents liquid starch-digesting enzyme from accessing milled material trapped in the dough ball and thus prevents the complete liquefaction of the slurry tank contents. Dough balls present a number of problems to an ethanol plant as they will clog the jet cooker and can clog other pipes that are used to transport the processed mash from one tank to another. Many ethanol plants employ a screening system to remove or filter dough balls out of the mash prior to entering the jet cooker. The screening system must be cleaned frequently and requires that the continuous flow of mash out of the slurry tank be diverted to a second set of piping while the screen is cleaned. Avoiding the formation of dough balls can be a significant savings to the ethanol plant as more plant material is available for hydrolysis and the complications to the jet cooker and other piping is avoided.

Starch-digesting enzyme delivered by a transgenic plant prevents the formation of dough balls that are stable enough to be detected in the effluent from the slurry tank. While not to be limited by theory, starch-digesting enzyme delivered by transgenic plant material allows for the integral association of the starch-digesting enzyme with the starchy substrate early in the milling process. Starch-digesting enzyme delivered through the addition of transgenic plant material effectively incorporates the starch-digesting enzyme into the milled plant material and facilitates the break-down of starch. Transgenic plant material expressing a starch-digesting enzyme can be combined with at least one other starchy plant material to prevent the formation of dough balls. The starch-digesting enzyme can be an alpha-amylase. The alpha-amylase can be 797GL3.

Transgenic plant material expressing a starch-digesting enzyme can be combined with at least one other starchy plant material to form an admix such that the transgenic plant material delivers an appropriate amount of starch-digesting enzyme to perform the starch hydrolysis process. The different plant materials may be combined by one or more process, including but not limited to, wet milling, dry milling, dry grinding, cracking, coarse grinding, fine grinding, fractionating, mixing, flaking, steam flaking, rolling and chopping. The starch-digesting enzyme can be an alpha-amylase. The alpha-amylase can be 797GL3. The admix can contain 0.1%, 0.2%, 0.3% 0.4% 0.5%, 1%, 1.5%, 2%, 2.5%, 3%, 3.5%, 4%, 4.5%, 5%, 6%, 7%, 8%, 9%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, 95% or 100% of the transgenic plant material expressing a starch-digesting enzyme.

The admix can contain transgenic plant material expressing at least one starch-digesting enzyme and at least one other starchy plant material. The other starchy plant material in the admix can be selected from the group consisting of non-transgenic plant material and transgenic plant material. It is envisioned that the transgenic plant material can be expressing any transgene such as an insect control gene, herbicide tolerance gene, nematode control gene, growth regulator, starch digesting enzyme, cellulose digesting enzyme, protease, phytase, and the like. The other starchy plant material can also be plant material from a plant source that is not transgenic. The other starch-containing plant material can be from a source (e.g., a plant strain) that is known to produce a relatively high level of fermentable sugars upon liquefaction and/or saccharification, or that has been bred or engineered to have some other advantageous property (e.g., pest or drought resistance). In some embodiments, more than two starch-containing plant materials can be used. Any combination of transgenic and nontransgenic plants can be used, so long as at least one plant material expresses a starch-digesting enzyme.

Conventional dry grind ethanol plants typically use approximately 29 to 33% solids in the slurry tank; however, when transgenic plant material expressing a starch-digesting enzyme is used in the mixture, the percentage of solids in the slurry tank can be increased to approximately 35 to 60% solids. While not to be limited by theory, the mechanism of delivering the enzyme through the transgenic plant material allows for increased solids to enter the processing system due to the intimate association of the enzyme with the substrate early in the milling process. Transgenic plant material expressing a starch-digesting enzyme can be combined with at least one other starch containing plant material such that the total solids entering the slurry tank is approximately 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59% or 60%. The starch-digesting enzyme can be an alpha-amylase. The alpha-amylase can be 797GL3.

The admix can be formed by mixing dry plant materials from different starch-containing plants together before wetting with the aqueous solution. It is also possible to form a mash by adding the different starch-containing plant materials sequentially or simultaneously to a vessel while an aqueous solution is being added. In some embodiments, the different plant materials can be grown together in a pre-determined ratio to provide a harvestable crop that can be used as the starch source for the presently disclosed process.

IV. Starch Hydrolysis Processes

In view of the increasing importance of ethanol fuels, improved processes for the hydrolysis of plant starch to fermentable sugars is highly desirable. For example, any improvement in the process that reduces time, expense, or energy expenditure or increases the quality of the resulting ethanol or another by-product of the ethanol production process is of interest.

Figure 1B:
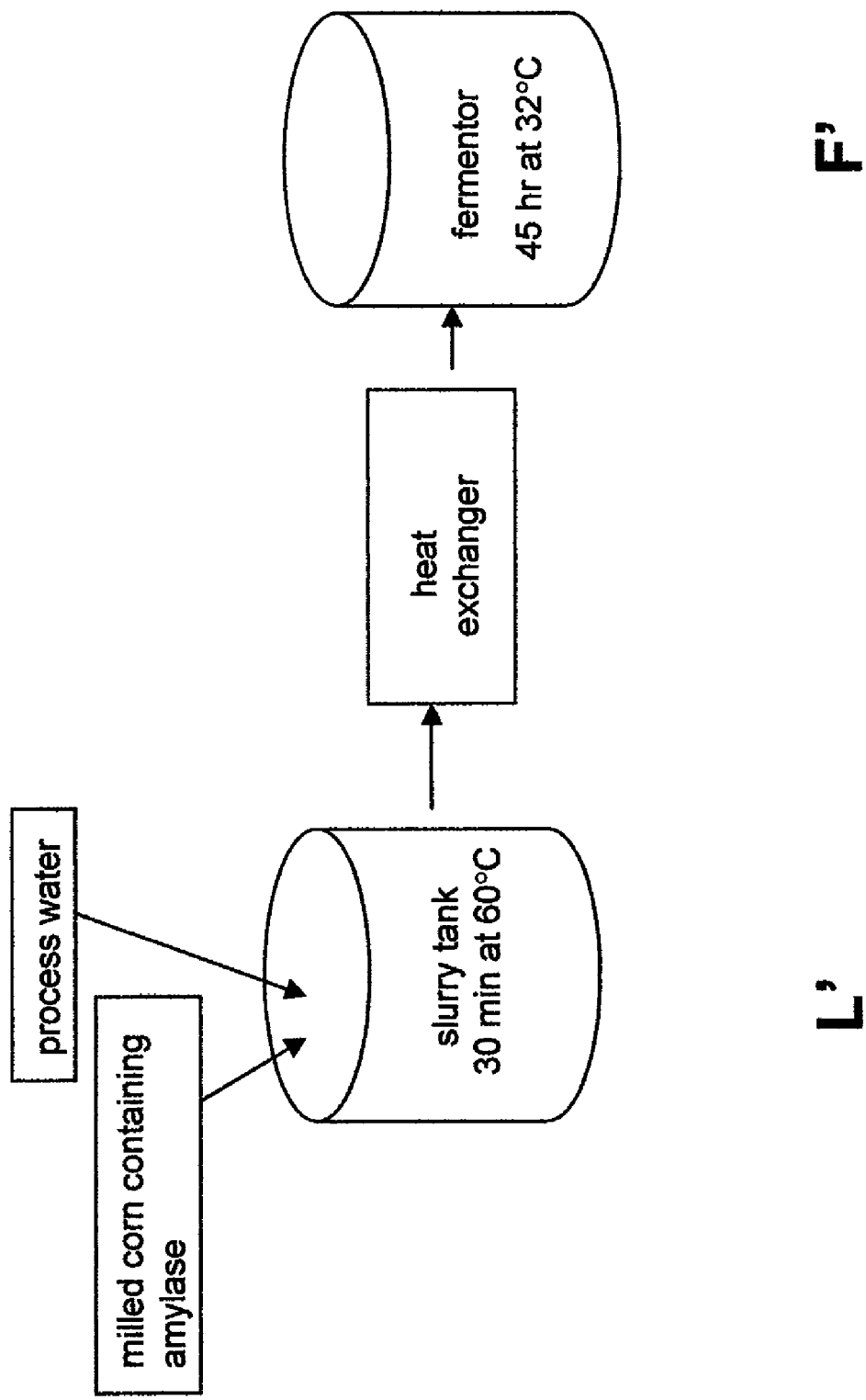
FIG. 1B is a schematic drawing showing a process of preparing ethanol according to the presently disclosed subject matter.

FIGS. 1A and 1B provide schematic illustrations comparing a conventional dry grind process for reducing starch (e.g., reducing corn starch to ethanol) (FIG. 1A) to a process of the presently disclosed subject matter (FIG. 1B). Referring particularly to FIG. 1A, the conventional process involves a pH adjustment taking place in liquefaction step L in a slurry tank which contains milled corn and process water. The pH of the slurry (after adding stillage is generally ~pH 4.8) is increased to pH 5.8 for optimal amylase activity. The process also involves jet cooking step JC (i.e., the steam injection/retention loop), wherein the slurry is heated to 105-120 degrees C. for about 8 minutes. Two amylase additions are included in the conventional process, one in liquefaction step L and one in secondary liquefaction step SL. In secondary liquefaction step SL, the slurry is heated to 90 degrees C. for 60 minutes. Following cooling (via heat exchange), the liquefact from secondary liquefaction step SL is fermented in fermentation step F for 50 hours at 32 degrees C. Prior to and/or during fermentation step F, the pH is adjusted down to pH 4.8.

IV. A Starch Liquefaction

The presently disclosed subject matter relates to a process of starch liquefaction that can be done at a low pH, for example, the natural pH of a slurry comprising a milled starch-containing plant material and water, or backset, or a combination thereof. See liquefaction step L' in FIG. 1B.

Because the starch liquefaction is performed at a lower pH, no pH adjustment is necessary, either as part of liquefaction step L' or at any point during an ethanol production process involving a liquefaction step L' (i.e., throughout the combination of liquefaction, saccharification, and fermentation steps used to produce ethanol). Thus, no pH-adjusting materials (e.g., bases or salts) are added to the slurry. In some embodiments, the presently disclosed starch liquefaction process can be performed more quickly than conventional liquefaction and at a lower temperature (e.g., without a secondary liquefaction step or a jet cooking step).

In some embodiments, then, the presently disclosed subject matter provides a process for starch liquefaction, wherein the process comprises (a) providing an aqueous slurry of a first starch-containing plant material, wherein the first starch-containing plant material is derived from a plant that expresses a starch-digesting enzyme; and (b) heating the slurry to a first temperature for a first period of time, thereby digesting starch in the slurry to form a starch liquefact, wherein the starch liquefaction is performed without making a pH adjustment. The resulting starch liquefact can comprise solubilized dextrinized starch, e.g., an oligosaccharide, a fermentable sugar, or a combination thereof.

The first starch-containing plant material can be generally derived from a plant expressing a heterologous enzyme. In some embodiments, the first starch-containing plant material is derived from a transgenic plant. Methods of preparing transgenic plants containing "self-processing" enzymes such as starch-digesting enzymes are disclosed in U.S. Pat. No. 7,102,057, herein incorporated by reference in its entirety.

The plant material can be from a plant that is normally used to produce ethanol or fermented products, such as wheat, barley, corn, rye, potato, grapes or rice. In some embodiments, the first starch-containing plant material is derived from a transgenic monocot plant or a transgenic dicot plant. In some embodiments, the transgenic monocot plant is selected from the group consisting of corn, rice, barley, wheat, sorghum, and millet. In some embodiments, the transgenic monocot plant is corn. In some embodiments, the transgenic dicot plant is selected from potato, sweet potato, and cassava.

IV.B. Viscosity

The viscosity of the slurry throughout the ethanol production process is a critical component of ethanol production. The continuous flow process for ethanol production requires that the slurry be low enough in viscosity to move through pumps and pipes at a continuous rate. A slurry that gets too viscous can plug pipes, overflow tanks and cause undue stress on pumping equipment. In addition, a slurry that is not viscous enough can also cause problems as the solids in the slurry can fall out of the slurry and build up in pipes and pumps which also can cause plugging problems or undue stress on equipment. Providing the starch-digesting enzyme through the use of transgenic plant material results in a slurry with a lower viscosity than typically observed when using liquid enzyme. The lowered viscosity of the slurry is observed through-out the ethanol production process starting with the viscosity of the mash as it is formed by mixing the meal with liquid, the viscosity of the mash as it enters the slurry tank, viscosity of the effluent from the slurry tank, viscosity after liquefaction is considered complete and viscosity after the effluent from liquefaction is cooled prior to entering the fermentation process.

Delivering the starch-digesting enzyme through transgenic plant material allows for the ethanol plant to adjust the ethanol production process so that the viscosity of the slurry remains at a desired level. The adjustments to the process can include but are not limited to increasing the percentage of solids used to create the mash, removing the addition of pH adjusting chemicals to the mash, decreasing the liquefaction time, removing the use of a jet cooker, and the like. The desired viscosity of the mash can be determined as outlined in Example 10 using an RVA-4 Viscometer. The desired viscosity can be anything less than about 4000 cP, 3500 cP, 3000 cP, 2500 cP, 2000 cP, 1500 cP, 1000 cP, 500 cP, 400 cP, 300 cP, 200 cP, 100 cP, or 50 cP and will vary depending on where in the ethanol production process the viscosity is measured.

A method for lowering the viscosity of a mash comprising an admix of transgenic plant material expressing a starch-digesting enzyme is envisioned. Combining transgenic plant material expressing at least one starch-digesting enzyme with any other starchy material is a method for lowering the viscosity of a mash to a desired viscosity. The method for lowering the viscosity of a mash can optionally further include the use of additional enzymes delivered either as transgenic plant material or delivered as liquid enzymes. The additional enzymes can be additional starch-digesting enzymes, cellulases, pectinases or any other enzyme.

The method for lowering the viscosity of a mash can be performed in about 2 minutes, 5 minutes, 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 80 minutes, 90 minutes, 100 minutes, 110 minutes, 120 minutes, 130 minutes, 140 minutes, 150 minutes, or 160 minutes.

The method for lowering the viscosity of a mash can be performed at about 32 degrees C., 37 degrees C., 42 degrees C., 47 degrees C., 52 degrees C., 57 degrees C., 62 degrees C., 67 degrees C., 72 degrees C., 77 degrees C., 82 degrees C., or 85 degrees C. The heating step of the liquefaction process can involve the use of temperatures below those used during conventional liquefaction processes (e.g., below about 95 degrees C. to 120 degrees C.).

In some embodiments, the first temperature ranges from about 60 degrees C. to about 85 degrees C. In some embodiments, the first temperature ranges from about 75 degrees C. to about 80 degrees C. In some embodiments, the liquefaction does not include a jet-cooking step. In some embodiments, the liquefaction does not include a secondary liquefaction step. Thus, the presently disclosed liquefaction method, in some embodiments, involves a single heating step.

In some embodiments the first period of time for liquefaction is less than about 90 minutes. In some embodiments, the first period of time for liquefaction ranges from about 20 minutes to about 35 minutes. In some embodiments, the first period of time for liquefaction ranges from 22 minutes to 30 minutes (e.g., can be about 22, 23, 24, 25, 26, 27, 28, 29, or 30 minutes).

The starch-digesting enzyme can be selected from the group consisting of α-amylase, glucoamylase, glucose isomerase, β-amylase, α-glucosidase, pullulanase, amylopullulanase, and combinations thereof. Indeed, the starch-digesting enzyme can be any enzyme that breaks down starch into smaller polysaccharides. In some embodiments, the starch-digesting enzyme is α-amylase. In some embodiments, the alpha-amylase is 797GL3.

IV.C. Liquefaction

In some embodiments, the presently disclosed subject matter provides a process for producing ethanol that includes a liquefaction step that takes place at a low pH and at reduced temperatures in comparison to conventional liquefaction methods. Referring again to FIG. 1B, the presently disclosed corn-to-ethanol process involves a simplified process, wherein, for example, amylase-containing corn and process water can be combined in a slurry tank in liquefaction step L' and heated for about 30 minutes at about 80 degrees C. No pH adjustment is made to the slurry during L'. In fermentation step F' the liquefact resulting from L' is transferred to a fermentor via a heat exchanger, where fermentation or SSF at 32 degrees C. produces ethanol.

A method for producing ethanol in which the mash is never heated to more than 10 degrees C. above the initial gelatinization temperature of the milled plant material prior to entering a fermentation stage is also envisioned. The initial gelatinization temperature is the lowest temperature at which gelatinization of the starch commences. Starch heated in water begins to gelatinize between 50 degrees C. and 75 degrees C.; the exact temperature of gelatinization depends on the specific starch, and can be readily determined by the skilled artisan. Thus, the initial gelatinization temperature may vary according to the plant species, to the particular variety of the plant species as well as with the growth conditions. In the context of the instant application, the initial gelatinization temperature of a given starch is the temperature at which birefringence is lost in 5% of the starch granules using the process described by Gorinstein, S et. al. Starch/Starke, vol 44(12): 461-466 (1992).

Generally, the mash will have a pH that is the natural pH of the slurry (i.e., the pH of the mixture of starch-containing plant material, water, and/or backset). As previously discussed, hereinabove, this mash can be used without the addition of any pH adjusting chemicals. In some embodiments, this mash has a pH of between about 3.5 and about 5.2; about 3.8 and about 4.7; about 4.0 and about 4.5. In some embodiments, the pH is about 4.8.

The process can further comprise a jet cooking step following the heating step. In some embodiments, the jet cooking comprises heating the effluent from the slurry tank to a temperature ranging from about 90 degrees C. to about 120 degrees C. for a period of time ranging from about 3 minutes to about 15 minutes.

In order to facilitate wetting or mixing the aqueous mash, the step of providing the aqueous mash can comprise holding the mash in a tank (i.e., a pre-slurry tank) for a period of time prior to the heating step. Any suitable mixing method can be used, including any suitable manual or mechanical mixing method that can be used in conjunction with the pre-slurry, slurry and liquefaction tanks. If the mash is prepared in a separate tank or vessel than that in which the heating will take place, the mash can be moved to the heating tank by any suitable approach (e.g., pouring, pumping, or the like).

In some embodiments, the starch liquefact prepared from the presently disclosed process has a dextrose equivalent (dextrose equivalents) of at least about 13. In some embodiments, the dextrose equivalents of the liquefact is between about 13 to about 17. Thus, the dextrose equivalents of the liquefact can be about 13, 14, 15, 16, or 17.

797GL3 amylase expressed in transgenic corn has been found to produce a distribution of oligosaccharides centered around DP7. Bacillus-derived amylases produce a bimodal distribution, with one peak at DP7, a substantial fraction greater than DP20, and some fragments as high as DP3900. Thus, in some embodiments, the starch liquefact comprises a uniform oligosaccharide distribution.

V. Process for Producing Ethanol

Fermentable sugar can be lost during high temperature, long hold times, and the use of only mildly acidic pH conditions. These losses can be attributed, at least in part, to Maillard reactions between a reducing end on the carbohydrate and an amino compound (e.g., ammonia or a protein). The Maillard reactions are known to be temperature, pH, and time dependent. Thus, reducing pH from the 5.8 typical for liquefaction to a lower pH (e.g., between 5.2 and 3.8) should decrease the amount of Maillard reaction products. Decreasing the time the slurry is held at high temperature should also decrease undesired degradation reactions. In particular, if the jet cooking step is not employed, a greater yield of fermentable sugars after liquefaction is expected. Coupled with the action pattern of the corn-expressed enzyme, these factors can lead to a substantially higher yield of ethanol from the presently disclosed process.

In some embodiments, the presently disclosed subject matter provides a process for producing ethanol that includes a liquefaction step that takes place at a low pH and at reduced temperatures in comparison to conventional liquefaction methods. Referring again to FIG. 1B, the presently disclosed corn-to-ethanol process involves a simplified process, wherein, for example, amylase-containing corn and process water can be combined in a slurry tank in liquefaction step L' and heated for about 30 minutes at about 80 degrees C. No pH adjustment is made to the slurry during L'. In fermentation step F' the liquefact resulting from L' is transferred to a fermentor via a heat exchanger, where fermentation or SSF at 32 degrees C. produces ethanol.

Prior to fermentation, the starch liquefact can be saccharified. The saccharification can include adding one or more additional starch-digesting enzymes to the starch liquefact. In some embodiments, the additional starch-digesting enzymes include glucoamylase. The amount of glucoamylase employed in the present process can vary according to the mixture of dextrins present in the starch liquefact. For example, if the starch liquefact is high in concentration of fermentable, small sugars, less glucoamylase might be needed. The saccharification process can further include a heating step, wherein the starch liquefact comprising additional starch-digesting enzymes (i.e., the saccharification mixture) is heated to a temperature (e.g., a temperature that allows for optimal activity for the enzymes employed) for a period of time.

In some embodiments, the fermenting involves a simultaneous saccharification and fermentation (SSF) step.

The saccharification and/or fermentation mixture can include additional ingredients to increase the effectiveness of the process. For example, the mixture can include added nutrients (e.g., yeast micronutrients), antibiotics, salts, added enzymes, and the like. Nutrients can be derived from stillage or backset added to the liquid. Suitable salts can include zinc or magnesium salts, such as zinc sulfate, magnesium sulfate, and the like. Suitable added enzymes include those added to conventional processes, such as protease, phytase, cellulase, hemicellulase, exo- and endo-glucanase, xylanase, pullulanase and the like. In some embodiments, the process comprises adding one or more reagents from the group consisting of an additional starch-digesting enzyme, a yeast extract, an antibiotic, and yeast to the starch liquefact.

As noted hereinabove, in some embodiments, the entire ethanol producing process takes place with no pH adjustment. Thus, in some embodiments, no salts are added during saccharification and/or fermentation. Eliminating pH adjustments can reduce the costs of purchasing and storing chemicals and can reduce the salt content of the intermediates (e.g., glucose) produced. The elimination of calcium containing salts can reduce the formation of "beer stone" and the costs associated with its removal.

In some embodiments, the fermenting comprises:
adding α-amylase to the starch liquefact;
cooling the starch liquefact to about 40 degrees C. to provide a cooled starch liquefact;

adding a yeast extract solution to the cooled starch liquefact;

adding an antibiotic solution to the cooled starch liquefact;

adding a solution of yeast to the cooled starch liquefact; and agitating the cooled starch liquefact at the second temperature for the second period of time.

In some embodiments the yeast is Ethanol Red yeast.

In some embodiments, the second temperature is from about 28 degrees C. to about 35 degrees C. In some embodiments, the second temperature is about 32 degrees C.

The product of the fermentation process can be referred to herein as "beer". For example, fermenting corn produces "corn beer". Ethanol can be recovered from the fermentation mixture (i.e., from the beer) by any of a variety of known processes. For example, ethanol can be recovered by distillation. Thus, in some embodiments, the presently disclosed process further comprises an ethanol recovery step. This step can comprise distillation.

The remaining stillage includes both liquid and solid material. The liquid and solid can be separated by, for example, centrifugation. The recovered liquid, thin stillage, can be employed as at least part of the liquid combined with milled plant material in the slurry tank. Use of a transgenic plant material to deliver the starch-digesting enzyme results in a stillage that contains less solid material than the stillage resulting from use of liquid enzyme.

The recovered solids, often referred to as distiller's dried grain (dried distiller grain), include unfermented grain solids and spent yeast solids. The thin stillage can be concentrated to a syrup, which can be added to the dried distiller grain and the mixture then dried to form distiller's dried grain plus solubles (dried distiller grain and solubles). Dried distiller grain and/or dried distiller grain and solubles can be sold as animal feed.

In some embodiments, the presently disclosed process produces a higher amount of ethanol than a conventional process. In some embodiments, the presently disclosed process produces ethanol more quickly during fermentation than a conventional process. In some embodiments, fermenting the starch liquefact provides a solution comprising at least about 10% (w/v) ethanol after about 20 hours. In some embodiments, fermenting the starch liquefact provides a solution comprising at least about 11.8% (w/v) ethanol after about 96 hours.

V.A. Simultaneous Liquefaction and Saccharification

Generally, liquefaction takes place at temperatures that are too high to allow for good activity of all the enzymes needed to fully reduce starch to fermentable sugars, such as glucose. In some embodiments, the presently disclosed subject matter further provides processes involving simultaneous liquefaction and saccharification. These processes also can be performed without adjusting the pH of the starch-containing slurry and can be done at relatively low temperatures compared with the liquefaction temperatures of conventional processes. For example, the simultaneous liquefaction and saccharification process can be done at a temperature low enough for good activity of enzymes generally used in saccharification processes, such as glucoamylases.

In some embodiments, the simultaneous liquefaction and saccharification process involves the use of at least two starch-digesting enzymes. For example, a first enzyme can degrade starch into smaller polysaccharides, while the other enzyme can digest the smaller polysaccharides into fermentable sugars, e.g., glucose. For example, thermostable α-amylase and glucoamylase can be used in the presently disclosed processes. In some embodiments, neither of the enzymes is expressed in a transgenic plant. In some embodiments, one or both enzymes can be provided to a starch slurry by being present in a transgenic plant material included in the mash.

In some embodiments, the presently disclosed process comprises:

providing an aqueous mash, said aqueous mash comprising:

a first starch-containing plant material, wherein the first starch-containing plant material is derived from a plant that expresses a first starch-digesting enzyme; and a second starch-digesting enzyme; and heating the aqueous mash to a first temperature for a first period of time, wherein liquefaction and at least partial saccharification of starch is accomplished without a pH adjustment, thereby providing a mixture containing glucose.

The first and second starch-digesting enzymes can include any combination of starch-digesting enzymes. In some embodiments, the first starch-digesting enzyme is α-amylase. In some embodiments, the second starch-digesting enzyme is glucoamylase The second starch-digesting enzyme can be derived from any source. Thus, the glucoamylase can be an enzyme produced by a microorganism, such as a known commercially available glucoamylase, or be derived from a transgenic plant. In some embodiments, the glucoamylase is derived from *Thermomyces lanuginosus*, and can be referred to as *Thermomyces lanuginosus* glucoamylase. The enzymatic activity of *Thermomyces lanuginosus* glucoamylase is described in Rao et al. Biochem J., 193, 370-387 (1981). In some embodiments, the glucoamylase is from a transgenic plant. Thus, in some embodiments, the aqueous mash can comprise a second starch-containing plant material that expresses glucoamylase or any other second starch-digesting enzyme.

In some embodiments, the mash can further comprise an additional starch-containing plant material which does not express a starch-digesting enzyme. This additional starch-containing plant material can be present in the mash when only a single starch-digesting enzyme-expressing plant material is present, or wherein two or more different starch-digesting enzyme-expressing plant materials are present.

The ratio of non-starch-digesting enzyme-expressing plant material and starch-digesting enzyme-expressing plant material can be present in any suitable ratio so that the amount of starch-digesting enzyme in the mash is sufficient to digest the starch to produce glucose in a suitable amount of time or to produce a mixture that contains a desired level of glucose. Similarly, the ratio of the different starch-digesting enzyme-expressing plant materials can be adjusted to facilitate a desired amount of saccharification in a desired amount of time. In some embodiments, the step of providing the mash comprises admixing the first starch-containing plant material and a second starch-containing plant material that does not express a glucoamylase to form a plant material mixture comprising between about 0.1% and about 100% of the first starch-containing plant material by weight. The plant material mixture can comprise between about 1% and about 30% or between about 5% and about 20% of the first starch-containing plant material (e.g., about 5%, 6%, 7%, 8%, 9%, 10%, 11%, 12%, 13%, 14%, 15%, 16%, 17%, 18%, 19%, or 20%). The mash can further comprise an aqueous solution (e.g., water, de-ionized water, backset (i.e., stillage), etc.). In some embodiments, more than two starch-containing plant materials can be used. Any combination of transgenic and nontransgenic plants can be used, so long as at least one plant material expresses a starch-digesting enzyme.

In some embodiments, the step of providing the aqueous mash can comprises wetting the starch-containing material (e.g., a single starch-containing material or two or more different starch-containing materials) for a period of time with an aqueous solution in a pre-slurry tank prior to the heating step.

In some embodiments, the first period of time ranges from about 5 minutes to about 90 minutes. In some embodiments, the first temperature ranges from about 60 degrees C. to about 75 degrees C. The temperature can be chosen to be compatible with thermostable glucoamylases, such as those derived from *Thermomyces lanuginosus* (i.e., *Thermomyces lanuginosus* glucoamylase).

In some embodiments, the heating step effects complete saccharification of the slurry. Thus, in some embodiments, approximately 80% to approximately 100% of the glucose expected from degradation of the starch in the slurry is produced during the heating step.

The glucose produced from a complete simultaneous liquefaction and saccharification process can be recovered by any suitable approach. In addition to glucose, the heated mash can comprise additional materials, such as oil, protein and fiber by-products of the simultaneous liquefaction and saccharification process. These materials can also have economic value and can be recovered, as well.

The recovered glucose can be prepared in any formulation suitable for fermentation (e.g. to alcohol). The amount of recovered glucose fed into a fermentor can be controlled so as to enhance the survival of the yeast in the fermentor. Alternatively, the glucose can be used in other products, e.g. as a sweetener, in sweetened foods, for intravenous solutions for use in hospitals or other medical settings. The glucose can also be used to prepare other chemicals. For example, the glucose can be treated with glucose isomerase to prepare fructose.

In some embodiments, the heating step effects partial saccharification of the mash. For example, heating can lead to a mixture containing at least some glucose and some larger dextrins. In some embodiments, the heating step can yield about 90%, 80%, 70%, 60%, 50%, 40%, 30%, 20%, or 10% of the theoretical amount of glucose expected from complete saccharification based upon the amount of starch initially present in the mash. In some embodiments, the heating provides about 10% saccharification of the mash. Thus, in some embodiments, the partial saccharification can provide about 10% of the expected amount of glucose expected based upon the amount of starch in the mash.

Subsequent fermentation of a partially saccharified mixture can be advantageous, in that it allows for control of the initiation, rate, and/or extent of fermentation activity during a SSF process. In particular, the quantity of different starch-containing plant materials and or enzymes can be adjusted to provide a suitable amount of glucose to enhance the survival of yeast during a subsequent fermentation of the mixture resulting from the simultaneous liquefaction and saccharification process. The amount of glucose being fed into a fermentation process can also affect the quality of co-products of the fermentation process, including dried distiller grain and dried distiller grain and solubles. Alternatively, the glucose resulting from a simultaneous liquefaction and saccharification process can be removed from the mixture and used for any desired purpose.

In some embodiments, the process can include a separate second saccharification step. For example, the process can comprise heating the mixture containing glucose to a second temperature for a second period of time, thereby effecting complete saccharification of the mixture. This second heating step can include the addition of additional enzyme, e.g., additional glucoamylase. In some embodiments, the mixture from a partial simultaneous liquefaction and saccharification process can be used in a fermentation wherein additional saccharification can take place during fermentation. Thus, in some embodiments both additional enzymes and yeast can be added to the mixture, thereby producing additional glucose and producing ethanol. In some embodiments, the glucose of the presently disclosed process can be used to produce an end product selected from the group consisting of an alcohol, lactic acid, an amino acid, fructose, citric acid, propanediol, dried distiller grain, dried distiller grain and solubles, or a combination thereof.

Delivery of the starch-digesting enzyme through the use of transgenic plants expressing the starch-digesting enzyme allows for significant changes to the process of producing fermentable sugars. A method for producing fermentable sugars from a mash comprising transgenic plant material expressing a starch-digesting enzyme wherein the transgenic plant material is tempered in a fluid, cracked to break apart the corn kernels, incubated in the tempering fluid at about 30 degrees, 35 degrees, 40 degrees, 45 degrees, 50 degrees, 55 degrees, 60 degrees, 65 degrees, 70 degrees, 75 degrees, 80 degrees, 85 degrees C. for about 2 minutes, 3 minutes, 4 minutes, 5 minutes, 10 minutes, 15 minutes, 20 minutes, 25 minutes or 30 minutes, and collecting the fermentable sugars is envisioned. The process may also comprise washing the solids recovered after collecting the fermentable sugars and drying the solids which can be used as an animal feed product. Another embodiment of the process further comprises fermenting the fermentable sugars to produce ethanol.

V.B. Products of Starch Reduction

In some embodiments, the presently disclosed subject matter provides a product such as, but not limited to, alcohol, lactic acid, an amino acid, fructose, citric acid, propanediol, dried distiller grain, dried distiller grain and solubles. In some embodiments, the product is an oil, a protein, or a fiber. These products can be primary or co-products (e.g., by-products) provided by the fermentation of a fermentable sugar. The product can also be any product that can be recovered from any stage of a liquefaction or simultaneous liquefaction and saccharification process.

In particular, dried distiller grain and dried distiller grain and solubles are economically important co-products of corn-to-ethanol production. Dried distiller grain and dried distiller grain and solubles are primarily used as animal feed. Recognized value attributes of dried distiller grain and solubles are: consistency, physical characteristics (e.g. flowability, color, odor), and composition (e.g. protein and fiber content). Improvements in dried distiller grain and solubles benefit ethanol producers, commodity marketers, and the animal production industry.

The quality of dried distiller grain and dried distiller grain and solubles is negatively impacted by prolonged process time and elevated temperature. Maillard reaction products are formed during high temperature process steps in corn-to-ethanol productions. The presence of Maillard reaction products negatively impacts the quality of dried distiller grain and dried distiller grain and solubles. The presently disclosed processes can result in reduced process time, reduced process temperature, or both. This in turn can reduce formation of Maillard reaction products and thus improve the consistency and physical characteristics of the dried distiller grain and dried distiller grain and solubles. In addition, the presently disclosed processes, particularly embodiments using amylase transgenic corn, can result in more complete digestion of starch, producing smaller starch fragments than bacterial alpha-amylases currently in use. These processes can result in higher protein content in the final dried distiller grain and solubles product.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

General Methods

Corn Flour: Corn flour was prepared by dry milling in a hammer mill through a 4/64ths screen. Standard (or regular) corn refers to Yellow #2 corn. Amylase transgenic corn refers to amylase-expressing transgenic corn. An initial sample of conventional Yellow #2 corn was tested with a test-strip kit (REVEAL®) from Neogen Corporation (Lansing, Mich., United States of America) for the presence of aflatoxins and found to be negative for the contaminant. The test kit can detect aflatoxin at concentrations as low as 20 ppb.

Samples of conventional yellow #2 corn and amylase transgenic corn corn feedstocks were taken and tested using near-infrared (near-infrared) spectroscopy (Perkent DA7000 using vendor supplied calibrations) for oil, protein starch and moisture content. Average results (based on a dry weight basis) are shown in Table 1, below. Average values from Yellow #2 corn are shown for comparison.

TABLE 1

Composition of Amylase transgenic corn expressed as weight percentage

| Material | Oil | Std Dev | Protein | Std Dev | Starch | Std Dev | Moisture | Std Dev |
|---|---|---|---|---|---|---|---|---|
| amylase transgenic corn | 4.42 | 0.14 | 9.59 | 0.08 | 72.43 | 0.47 | 13.82 | 0.03 |
| Yellow #2 Corn | 4.42 | 0.07 | 9.72 | 0.14 | 72.15 | 0.28 | 12.91 | 0.30 |

Chemicals and Enzymes: "Ethanol Red" yeast (Product Code 42138 from Fermentis, Marcq-en-Baroeul, France) was used in fermentations in view of its high ethanol tolerance in the production of industrial ethanol from grain. The antibiotic Bactinex V50 was obtained from NABC (Atlanta, Ga., United States of America). Bactinex V50 is a blended product containing virginiamycin, low pH penicillin, and streptomycin and is effective against a wide array of both gram positive and gram negative bacteria. Commercial enzymes used included glucoamylase from *Aspergillus niger* and alpha-amylase from *Bacillus licheniformis*, both in liquid form. Sulfuric acid (93% by weight) was obtained from Ashland Specialty Chemical Company (Dublin, Ohio, United States of America). Aqueous ammonia (50%) for pH adjustment and caustic soda solution (NaOH in $H_2O$) for cleaning were obtained from GS Robins and Company (St. Louis, Mo., United States of America). The caustic soda solution was diluted to 2-5% (by weight) prior to use.

Slurry Tank Set Up: Slurry tank TA-1230 starts with 135 gallons of water and can hold 135 gallons of slurry throughout a run (~32% level, automatically controlled. Slurry tank TA-0990 holds 66 gallons of slurry throughout a run (~63% level, automatically controlled). The pre-mix tank (TA-0440) can hold 650 gallons of slurry throughout the process (~20% level, manually controlled). Once the first transgenic corn expressing alpha-amylase is mixed in the pre-mix tank, the cold slurry is slowly pumped into the slurry tank at the same time that the jet cooker is started on hot water from the slurry tank. The jet cooker is started on water and slowly transitioned to slurry. The pre-mix tank is held at 85 degrees F. (i.e., ~29.4 degrees C.) and ~20% level. The jet cooker was run at 3.0 gpm (gallons per minute) and 225 degrees F. (i.e., 107.2 degrees C.) with a back pressure set point of 9.0 psi (pounds per square inch), unless otherwise indicated.

Fermentation conditions: Unless otherwise noted, fermentation samples (i.e., mash or liquefact) were collected from the post-jet cook tube in a sterile container and dispensed into pre-weighed 1-liter flasks and or 250 milliliter Erlenmeyer flasks. 600 milliliter of the mash is dispensed into a 1-liter flasks and 110 milliliter into 250 milliliter flasks. The flasks are placed into a waterbath at 85 degrees C. and incubated for 45 minutes. After 45 minutes the flasks were placed in cool water to bring the temperature down to about 40 degrees C.

One sample was used to determine the amount of acid or base needed to adjust the pH to 4.80. If necessary, for example in control samples where liquefaction was carried out using conventional methods at pH 5.8, pH was lowered by the addition of 10 N sulfuric acid. To raise pH, 50% sodium hydroxide is added. The pH of all the flasks was adjusted to 4.80.

Yeast extract solution (0.4 g/milliliter) was added at 5.76 milliliter/100 g dry flour. Glucoamylase was added according to manufacturer's recommended dosage. A 10 mg/milliliter V50 antibiotic solution was added to reach 5 ppm in each flask. Four grams of Ethanol Red yeast were added into 18.5 milliliter of sterile de-ionized water (at 40 degrees C.) in a sterile centrifuge tube, mixed, and incubated at 40 degrees C. for 15 minutes. 2.4 milliliter yeast solution was then added into each flask, resulting in a starting yeast concentration of 15 millimolar/milliliter. The flasks were covered with rubber stoppers, with a syringe needle in place to allow venting of $CO_2$, and placed in an incubator/shaker at 32 degrees C. and allowed to ferment.

Example 2

Comparative Example 3% Amylase Transgenic Corn (Amylase Transgenic Corn) Admix Liquefaction at pH 5.8

Liquefaction of a 3% amylase transgenic corn admixture (admix) was performed using the industry standard liquefaction pH of 5.8. The total admix of corn flour and water contained flour prepared from 2260 lbs regular (i.e., standard) ground corn and 70 lbs ground amylase transgene corn (amylase transgenic corn), along with 500 gallons of water. Flow rates into the pre-slurry tank were: water: 2.0 gpm; standard corn: 543 lb/hr; amylase transgenic corn: 17 lb/hr. Slurry tank TA-1230 was used. The slurry tank pH was adjusted to 5.8. The temperature of slurry tank was 185 degrees F. (85 degrees C.). The slurry tank resident time was 45 minutes.

The jet cooker was run for 2.5 hours. After the 2.5 hours, the slurry completely replaced the water in the slurry tank (slightly more than three tank turnovers). Aliquots for fermentation were drawn after the 2.5 hour jet cooking flush.

Slurry samples, taken in triplicate (5 minutes apart), were removed from the slurry tank at the beginning, middle and end of the jet cooking flush and tested for pH, brix (i.e., soluble carbohydrates) and percent solids. Slurry samples for measurement of dextrose equivalents (dextrose equivalents), viscosity and trial fermentation were taken in triplicate, as well, after the end of the 2.5 hour jet cooking flush. Dextrose equivalents can be calculated, for example, using the Fehlings titration method, which is based on the reduction of cupric ion to cuprous ion in the presence of reducing sugars. The cuprous ion reduces iodide in acidic media, producing tri-iodide ions, which can be titrated with sodium thiosulfate. Titers of unknown samples can be compared to a standard to provide a relative dextrose equivalents value.

Table 2 shows the ethanol yield (v/v %) vs. fermentation time for each of the three replicate slurry samples taken for trial fermentation, in addition to the average ethanol yield of the three replicates.

TABLE 2

Ethanol Yield (v/v %) from the 3% Admix Liquefaction Samples

| Hour | Replicate 1 | Replicate 2 | Replicate 3 | Average |
|---|---|---|---|---|
| 6 | 6.11 | 6 | 6 | 6 |
| 22 | 7.4 | 7.3 | 7.4 | 7.4 |
| 34 | 9 | 9.4 | 9.1 | 9.2 |
| 40 | 10.2 | 10.3 | 10.1 | 10.2 |
| 46 | 10.7 | 10.7 | 10.5 | 10.6 |
| 58 | 11 |  | 11.2 | 11.1 |
| 64 | 11.3 | 11.3 | 11.3 | 11.3 |
| 70 | 11.5 | 11.3 | 11.5 | 11.4 |
| 100 | 11.5 | 11.4 | 11.6 | 11.5 |

Example 3

10% Amylase Transgenic Corn (Amylase Transgenic Corn) Admix Liquefaction at pH 4.8

Low pH Liquefaction of a 10% admix of amylase transgenic corn corn was examined. After the final aliquots described above in Example 2 were drawn, 180 lbs of amylase transgenic corn corn and 40 gallons of water were added to the pre-slurry tank all at once. Thereafter, the flow rates into the pre-slurry tank were changed to standard corn: 504 lb/hr; amylase transgenic corn corn: 56 lb/hr; water: 2.0 gpm. The pH of the slurry tank was adjusted to 4.8.

The jet cooker was run for 2.5 hours after the changes in flow rates. After the 2.5 hours the 10% admix slurry had completely replaced the 3% admix (slightly more than three tank turnovers). Slurry samples, in triplicate (five minutes apart), were taken from the slurry tank at the beginning, middle and end of the jet cooking flush and tested for pH, brix, and percent solids. After the 2.5 jet cooking stage, three replicate aliquots for fermentation were drawn.

Table 3 below shows the ethanol yield (v/v %) of the three replicates after various fermentation times. The average ethanol yield is also listed. Slurry samples for dextrose equivalents and viscosity were taken in triplicate immediately prior to the aliquots taken for fermentation.

TABLE 3

Ethanol Yield (v/v %) from the 10% Admix, Low pH Liquefaction Samples

| Hour | Replicate 1 | Replicate 2 | Replicate 3 | Average |
|---|---|---|---|---|
| 12 | 5.1 | 5.1 | 5.0 | 5.1 |
| 18 | 6.9 | 6.8 | 6.7 | 6.8 |
| 30 | 8.8 | 8.6 | 8.9 | 8.8 |
| 36 | 10.5 | 11 | 10.1 | 10.5 |
| 54 |  | 11.3 | 11.4 | 11.4 |
| 59 | 11.9 | 11.8 | 11.9 | 11.9 |
| 66 |  | 12 | 12 | 12 |
| 72 | 11.9 | 12.1 | 12.2 | 12.1 |
| 96 | 12.1 | 12.1 | 12.3 | 12.2 |

Example 4

20% Amylase Transgenic Corn (Amylase Transgenic Corn) Admix Liquefaction at pH 4.8

A slurry was prepared as a barnylase transgenic corn using 136 lbs standard corn flour, 34 lbs of amylase transgenic corn, and 49 gallons of backset. Backset was added first, then corn. The slurry tank conditions (using slurry tank TA-0990) were as follows: pH was 4.8; temperature was 85 degrees C.; and slurry tank residence time was 22 minutes. Flow rates into the slurry mixer were: backset=2.2 gpm; standard corn=368 lb/hr; and amylase transgenic corn corn: 92 lb/hr. The jet cooker was run for 90 minutes. After 90 minutes, fresh slurry was completely replaced the starting material in the slurry tank (slightly more than three tank turnovers) and aliquots for fermentation were taken.

Slurry samples were taken (in triplicate, 5 min apart) from the slurry tank at the beginning, middle and end of the jet cooking flush and tested for pH. Slurry samples for dextrose equivalents, viscosity and % solids were taken in triplicate immediately prior to drawing aliquots for fermentation.

Example 5

12% Amylase Transgenic Corn (Amylase Transgenic Corn) Admix Liquefaction at pH 4.8

After the fermentation aliquots were drawn as described in Example 4, the flow rates were changed to standard corn: 405 lb/hr and amylase transgenic corn corn: 55 lb/hr. Slurry tank conditions (using slurry tank TA-0990) for liquefaction of the 12% admix were as follows: pH was 4.8; temperature was 85 degrees C.; and slurry tank residence time was 22 minutes. The jet cooker was run for 90 minutes. After 90 minutes, fresh slurry had completely replaced the starting material in the slurry tank (slightly more than three tank turnovers). Fermentation aliquots were collected.

Slurry samples were taken (in triplicate, 5 min apart) from the slurry tank at the beginning, middle and end of the jet cooking flush and tested for pH. Slurry samples for dextrose equivalents, viscosity and % solids were taken in triplicate immediately prior to drawing aliquots for fermentation.

Example 6

8% Amylase Transgenic Corn (Amylase Transgenic Corn) Admix Liquefaction at pH 4.8

After the fermentation aliquots were drawn as described in Example 5, the flow rates were changed to standard corn: 423 lb/hr and amylase transgenic corn corn: 37 lb/hr. Slurry tank conditions (using slurry tank TA-0990) for liquefaction of the 8% admix were as follows: pH was 4.8; temperature was 85 degrees C.; and slurry tank residence time was 22 minutes. Again, the jet cooker was run for 90 minutes. After 90 minutes, fresh slurry was completely replaced the starting material in the slurry tank (slightly more than three tank turnovers). Aliquots for fermentation were drawn.

Slurry samples were taken (in triplicate, 5 min apart) from the slurry tank at the beginning, middle and end of the jet cooking flush and tested for pH. Slurry samples for dextrose equivalents, viscosity and % solids were taken in triplicate immediately prior to drawing aliquots for fermentation.

The jet cooker was run for an additional 60 minutes. After the 60 minutes, additional aliquots for fermentation were taken. Some aliquots were drawn from the end of the cook tube. Some aliquots were taken from the slurry tank prior to the jet cooker. These samples provided additional replicate samples of an 8% admix liquefact and samples of an 8% admix liquefact that that had not undergone jet cooking.

Example 7

Comparative Example of 0% Admix Liquefaction at pH 5.8

After all of the fermentation aliquots were drawn as described in Example 6, the flow rates were changed to standard corn: 460 lb/hr and amylase transgenic corn corn: 0.0 lb/hr. Alpha-amylase enzyme was added at a flow rate of 154 g/hr. The pH of the slurry was adjusted to 5.8. Thus, slurry tank conditions (using slurry tank TA-0990) were as follows: pH was 5.8; temperature was 85 degrees C.; and slurry tank residence time was 22 minutes. The jet cooker was run for 90 minutes. After 90 minutes, fresh slurry had completely replaced the starting material in the slurry tank (slightly more than three tank turnovers). Fermentation aliquots were drawn.

Slurry samples were taken (in triplicate, 5 min apart) from the slurry tank at the beginning, middle and end of the jet cooking flush and tested for pH. Slurry samples for dextrose equivalents, viscosity and % solids were taken in triplicate immediately prior to drawing aliquots for fermentation.

Example 8

Results of 20%, 12%, 8%, and 0% Admix Liquefaction

Table 4 shows the average percent dry solids (% DS) and dextrose equivalent (dextrose equivalents) numbers of samples taken from each of the admix liquefacts described above in Examples 4-7.

TABLE 4

Slurry Conditions Immediately Before Fermentation

| Condition | Example # | pH | % DS | dextrose equivalents | Post cook tube hold time at 85 degrees C. |
|---|---|---|---|---|---|
| 20% Admix | 4 | 4.8 | 34.5 | 16.1 | 0 |
| 12% Admix | 5 | 4.8 | 33.0 | 15.4 | 0 |
| 8% Admix | 6 | 4.8 | 33.0 | 14.8 | 0 |
| 8% Admix | 6 | 4.8 | 34.3 | 13.9 | 0 (replicate) |
| 8% Admix | 6 | 4.8 | 32.6 | 14.5 | No Jet Cook |
| 0% Admix | 7 | 5.8 | 34.7 | 13.6 | 45 |

Table 5 lists the average ethanol content (in % w/v) of the fermented sample after 96 hours of fermentation.

TABLE 5

Average Ethanol Content at 96 Hours

| Condition | Example # | EtOH (%, w/v) | Standard Deviation |
|---|---|---|---|
| 20% Admix | 4 | 12.26 | 0.07 |
| 12% Admix | 5 | 12.09 | 0.12 |
| 8% Admix | 6 | 11.92 | 0.02 |
| 8% Admix (Replicate) | 6 | 11.81 | 0.04 |
| 8% Admix (No Jet Cook) | 6 | 11.94 | 0.04 |
| 0% Admix | 7 | 11.63 | 0.03 |

Based on the final ethanol content, the 20% admix liquefact produced the most alcohol. Lowering the admix to 8% resulted in a slight decrease in the amount of ethanol produced. The 8% admix without jet cooking preformed as well as conditions that included jet cooking. The sample containing commercial amylase produced the least amount of ethanol.

Table 6 lists the average residual sugar content after 96 hours of fermentation. Total sugar level is the sum of the speciated sugar levels detected during HPLC analysis (e.g., glucose, DP2, DP3, and DP4+). Levels below 0.2% were below detection and counted as 0.1%.

TABLE 6

Average Residual Sugar Content at 96 Hours

| Condition | Example # | Total residual sugars (%, w/v) | Standard Deviation |
|---|---|---|---|
| 20% Admix | 4 | 0.95 | 0.03 |
| 12% Admix | 5 | 0.94 | 0.05 |
| 8% Admix | 6 | 1.03 | 0.01 |
| 8% Admix (Replicate) | 6 | 1.10 | 0.03 |
| 8% Admix (No Jet Cook) | 6 | 1.19 | 0.04 |
| 0% Admix | 7 | 0.90 | 0.01 |

The commercial amylase liquefact from Example 7 left the smallest amount of residual sugar, while the liquefact without jet cooking from Example 6 left the largest amount of residual sugars.

Final ethanol yield calculations were performed on the fermentors from all of the liquefaction conditions in Examples 4-7 and are listed in Table 7. The theoretical yield calculations compare measured ethanol content to the ideal case where 100% of the initial starch is converted to ethanol. Percent yield and standard deviation values are based on the average of triplicate fermentations at 96 hours.

TABLE 7

Yield Calculations

| Condition | Example # | Theoretical Yield (g/100 milliliter) | Actual Yield (g/100 milliliter) | % Yield | Standard Deviation |
|---|---|---|---|---|---|
| 20% Admix | 4 | 14.1 | 12.3 | 87.2 | 0.5 |
| 12% Admix | 5 | 13.4 | 12.1 | 90.3 | 0.9 |
| 8% Admix | 6 | 13.4 | 11.9 | 88.8 | 0.1 |

TABLE 7-continued

Yield Calculations

| Condition | Example # | Theoretical Yield (g/100 milliliter) | Actual Yield (g/100 milliliter) | % Yield | Standard Deviation |
|---|---|---|---|---|---|
| 8% Admix (Replicate | 6 | 13.9 | 11.8 | 84.9 | 0.3 |
| 8% Admix (No Jet Cook) | 6 | 13.2 | 11.9 | 90.2 | 0.3 |
| 0% Admix | 7 | 14.1 | 11.6 | 82.3 | 0.2 |

The admix conditions of 20%, 12% and 8% show nearly equivalent yields. The lack of jet cooking does not appear to adversely affect yield.

Example 9

Simultaneous Liquefaction and Saccharification

Corn flour from transgenic grain expressing the alpha-amylase 797GL3 was mixed with flour from commodity grain to achieve a final dose of approximately 54 microgram alpha-amylase/gram flour. This flour mixture was incubated with glucoamylase (glucoamylase) from *Thermomyces lanuginosus* (*Thermomyces lanuginosus* glucoamylase, produced in *Pichia*) at doses of 100 to 250 microgram glucoamylase/gram flour and at a flour:water ratio of 1:2. Assuming a moisture content of the flour of ~15%, this slurry contained 28% solids. Using a starch content value of 71% (measured in commodity grain by near-infrared), the theoretical 100% glucose yield of the reaction is 221 mg/milliliter. Rhizopus glucoamylase purchased from Wako was used as a control. Glucose content of syrups was measured using a glucose oxidase/horseradish peroxidase assay with 2,2'-azino-bis(3-ethylbenzylthiazoline-6-sulphonic acid) (ABTS).

Table 8 shows the glucose concentrations (in mg/milliliter) in syrups incubated for two hours at 70 degrees C., 80 degrees C., and 90 degrees C. with 100 microgram *Thermomyces lanuginosus* glucoamylase/g flour or 145 microgram Rhizopus glucoamylase/g flour. Table 9 shows the glucose concentrations of syrups incubated for 1.5 hours at 60 degrees C., 65 degrees C., 70 degrees C., or 75 degrees C. using either no glucoamylase, 250 microgram *Thermomyces lanuginosus* glucoamylase, or 364 microgram Rhizopus glucoamylase/g flour, both with alpha-amylase (AA+) or without alpha-amylase (AA−).

TABLE 8

Syrup glucose concentrations (mg/milliliter) after 2 hours

|  | No glucoamylase | Rhizopus glucoamylase | Thermomyces lanuginosus glucoamylase |
|---|---|---|---|
| 70 degrees C. | 7.8 | 9.6 | 198 |
| 80 degrees C. | 4.1 | 5.8 | 83 |
| 90 degrees C. | 3.5 | 6.4 | 21 |

TABLE 9

Syrup glucose concentrations (mg/mL) after 1.5 hours

|  | AA+ No GA | AA− NoGA | AA+ Rhizopus GA | AA− Rhizopus GA | AA+ TIGA | AA− TIGA |
|---|---|---|---|---|---|---|
| 60° C. | 10.5 | 8 | 20 | 19 | 40.5 | 35.5 |
| 65° C. | 10 | 6.5 | 18 | 14.5 | 45.5 | 38 |
| 70° C. | 7 | *** | 9 | *** | 192.5 | 93.5 |
| 75° C. | 13 | 4.5 | 18.5 | 16 | 196.5 | 70 |

*** denotes reactions from which syrup could not be obtained due to gelatinization.

Example 10

Slurry Tank Viscosity

Samples from the Slurry Tank:

Corn amylase was used as the enzyme delivery system for alpha-amylase in a production scale ethanol plant. Corn amylase was ground using a hammer mill (ICM). Other starch containing plant material was ground separately also using a hammer mill. The ground corn amylase and the ground other starch containing plant material were combined with stillage (approximately 15% to approximately 40% of the liquid added to the ground plant material), water in a ribbon mixer (ICM). The percentage of corn amylase in the flour varied from 3% to 4%. The corn amylase and conventional corn were combined with liquid to produce a slurry that averaged from about 33% to about 36% solids. The pH of the slurry was adjusted with the addition of ammonia and ranged from about pH 4.8 to pH 5.6. In some experiments, no ammonia was added to the slurry. The slurry from the ribbon mixer flowed into a continuous flow slurry tank held at approximately 85 degrees C. On average, a sample that enters the ribbon mixer takes about 25 minutes to exit the slurry tank. The viscosity of the slurry tank was measured using two different assays, the RVA-4 Viscometer and the funnel test.

Initially, corn amylase was added to the slurry tank as described above while continuing to add liquid amylase to the ribbon mixer. The amount of liquid amylase added to the ribbon mixer was slowly decreased and was eventually stopped entirely. The process of shutting off liquid amylase addition to the ribbon mixer took approximately 1 hour and 15 minutes. The viscosity of a slurry processed with liquid alpha-amylase after approximately 25 minutes at 85 degrees C. is approximately 90 seconds to 150 seconds when measured using the funnel test. Viscosity data collected during the 3 hr transition from liquid amylase to liquid amylase plus corn amylase to corn amylase alone is outlined in Table 10. This data demonstrates that delivery of the alpha-amylase through transgenic plant material reduces the viscosity of the contents of the slurry tank to well below the viscosity achieved when using liquid amylase.

Viscosity data collected with corn amylase alone is outlined in Table 11. This data demonstrates that when corn amylase is delivered solely through the use of transgenic corn expressing alpha-amylase, the viscosity of the slurry tank contents is much lower than is typically observed when using liquid alpha-amylase.

Determination of Viscosity Using the RVA-4 Viscometer:

Using a Newport Scientific Rapid Visco Analyser Series 4 (RVA-4), viscosities of samples from the slurry tank and liquefaction tank were measured. Approximately 500 ml of samples were drawn from each tank port into insulated containers (i.e. thermos). The sample was taken back to the lab and immediately processed.

The thermos was shaken vigorously for approximately 15 seconds. 25 g of sample was then poured into an RVA vessel. A paddle was added to the vessel and was placed on the RVA. The RVA-4 was set up to hold the sample at 85° C. for 6 minutes at a constant paddle rate of 160 rpm. Data was then exported to an Excel file.

Determination of Viscosity Using the Funnel Flow Test:

A 1 liter funnel was fitted with 12 inches of tubing with an inner diameter of 0.5 inches. A plug was added at the end of the tubing to retain the sample while filling the funnel. Approximately 1.2 liters of sample was added to the funnel. The plug was then immediately removed to allow the sample to begin to flow. The time it took for the sample to empty from the funnel and tube was recorded.

Method of Determining Percentage of Solids in the Slurry Tank Using the uWave Moisture Reader A Sartorius Microwave Loss-On-Drying Analyzer was used to determine the solids content of both liquefaction samples and slurry samples. Approximately 300 ml of sample was taken from the liquefaction or slurry tank in a 500 ml Nalgene plastic bottle. Two 4 inch sample pads were placed on the uWave and scale was reset to zero (i.e. tared). The sample bottle was shaken for 15 seconds; the correct amount of sample was then added to the sample pads using a Fisher-brand transfer pipette (cat. no. 13-711-7M) with the tip cut off to allow for a more representative sample. The sample was compressed between the 2 sample pads and the correct procedure below was used to determine solids content.

uWave Slurry Procedure:
Units: % S
Weights: 1.25-1.75: YES
Power: 60% 80 sec. 60%
Slope: 15 sec. 2 ppt
PreDry: NO
Test Mode: NORMAL uWave Liquefaction Procedure:
Units: % S
Weights: 1.50-1.75: YES
Power: 70% 80 sec. 60%
Slope: 15 sec. 2 ppt
PreDry: NO
Test Mode: NORMAL

TABLE 10

Viscosity of slurry tank during transition from liquid amylase to liqiud amylase plus corn amylase to corn amylase alone. Corn amylase was used at 10% admix.

| Time (hours and minutes) | Funnel time (seconds) | Percentage of solids (%) |
|---|---|---|
| 7:13 | 119 | |
| 7:17 | 121 | 32.20 |
| 7:21 | 128 | |
| 7:27 | 92 | |
| 7:29 | 70 | |
| 7:33 | 42 | |
| 7:34 | 31 | |
| 7:36 | 26 | 32.50 |
| 7:38 | 38 | |
| 7:41 | 21 | |
| 7:42 | 19 | |
| 7:44 | 19 | |
| 7:46 | 18 | |
| 7:50 | 17 | |
| 7:53 | 16 | |
| 7:58 | 16 | |
| 8:30 | | |
| 8:45 | | |
| 8:50 | 13 | |

TABLE 10-continued

Viscosity of slurry tank during transition from liquid amylase to liqiud amylase plus corn amylase to corn amylase alone. Corn amylase was used at 10% admix.

| Time (hours and minutes) | Funnel time (seconds) | Percentage of solids (%) |
|---|---|---|
| 8:53 | 13 | |
| 8:56 | | |
| 8:59 | | |
| 9:10 | | 33.93 |
| 10:15 | 13 | |

* slurry tank was maintained at a pH of approximately 5.8

TABLE 11

Viscosity of slurry tank with corn amylase as sole source of alpha-amylase enzyme.

| Percentage solids | RVA-4 viscometer (cP) | % CA admix | Funnel test time (seconds) | Sample name | pH of the slurry |
|---|---|---|---|---|---|
| 32.71 | 279 | 3 | 24 | wpe65 | 5.8 |
| 32.03 | 287 | 3 | 25 | wpe67 | 5.8 |
| 32.91 | 279 | 3 | 22 | wpe69 | 5.8 |
| 33.38 | 269 | 3 | 21 | wpe72 | 5.8 |
| 33.75 | 267 | 3 | 21 | wpeliq75 | 5.8 |
| 33.81 | 303 | 3 | 26 | wpe77 | 5.1 |
| 33.81 | 217 | 10 | 13 | 85 | 5.1 |
| 33.69 | 345 | 3 | 31 | wpe96 | 5.8 |
| 34.47 | 326 | 3 | 30 | wpe99 | 5.8 |
| 35.5 | 546 | 3 | 42 | wpe140 | 5.8 |
| 35.5 | 434 | 3 | 36 | wpe142 | 5.8 |
| 36.1 | 583 | 3 | 47 | wpe144 | 5.8 |
| 36.7 | 425 | 3 | 54 | wpe148 | 5.8 |
| 36.5 | 541 | 3 | 90 | wpe162 | 5.8 |
| 36.5 | 486 | 3 | 128 | wpe163 | 5.8 |
| 36.5 | 421 | 3 | 34 | wpe169 | 5.8 |

Example 11

Viscosity After Liquefaction

Corn amylase was used as the sole source of alpha-amylase in a dry grind ethanol production plant. The corn amylase was added to other starch containing plant material and processed through the slurry tank as described in Example 10. The process is a continuous flow process meaning that plant material is constantly added to the slurry tank and effluent from the slurry tank is always leaving the slurry tank. The slurry leaving the slurry tank is first transported through a jet cooker and then it is pumped into a liquefaction tank. The jet cooker and associated cook tube heat the slurry to approximately 106 degrees C. and apply a physical pressure to the slurry in order to facilitate gelatinization. The liquefaction tank is also a continuous flow tank with incoming slurry and out-going slurry happening constantly. Material entering the process at the ribbon mixer takes approximately 2.5 hours before exiting the liquefaction tank. The liquefaction tank is held at 85 degrees C. Slurry leaving the liquefaction tank is processed through a heat exchanger to cool the slurry before entering the fermentation tanks which are batch tanks and not continuous flow tanks.

The viscosity of the slurry exiting the liquefaction tank was measured as described in Example 10. The viscosity data is presented in Table 12. This data demonstrates that delivery of the alpha-amylase enzyme through transgenic corn grain incorporated at the slurry tank lowers the viscosity of the liquefaction tank to a level that is below that achieved by the use of liquid amylase. In addition, delivery of the alpha-amylase through the use of transgenic corn grain effectively eliminates the second addition of alpha-amylase which is typically performed after the jet cooker.

TABLE 12

Viscosity of samples from the liquefaction tank

| Percentage solids | RVA-4 viscometer (cP) | % CA admix | Funnel test time (seconds) | Sample name |
|---|---|---|---|---|
| 33.17 | 188 | 3 | 11 | wpe97 |
| 33.45 | 218 | 3 | 11 | wpe100 |

Example 12

Viscosity After Cooling Post Liquefaction Slurry

After liquefaction of a mash is considered complete, the mash is cooled to about ambient temperature by passing through a heat exchanger. The process of cooling the mash can lead to a thickened mash that becomes difficult to pump or move. A lab scale version of liquefaction can be established where an admix of corn grain expressing alpha-amylase is combined with conventional corn. The percentage of corn amylase in the admix will be varied. In addition, the total percentage of solids entering the liquefaction will be varied. The resulting mash generated by combining the corn grain admix with liquid will be adjusted to pH 3.2 to pH 5.8 and heated to 85 degrees C. for approximately 25 minutes to 150 minutes. A sample of the liquefied mash will be placed into the RVA-4 Viscomer. The RVA-4 Viscometer can be used to mimic the conditions of the heat exchanger following the method described in Example 10 with the following modifications. The RVA-4 Viscometer can be held at 85 degrees C. for 7 minutes followed by a transition to 27 degrees C. over 5 minutes. The subsequent changes in viscosity of the mash during the temperature change will be measured in the RVA-4 Viscometer as described in Example 10. Alpha-amylase delivered through the use of transgenic corn grain expressing alpha-amylase can produce a hydrolyzed starch product or liquefact that when cooled, is still low enough in viscosity to be easily moved from the heat exchanger into the fermentation tank.

A similar experiment will be performed to determine the viscosity of a cooled liquefaction mash wherein the transgenic corn amylase is replaced with the addition of liquid amylase.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of reducing the viscosity of a mash comprising the steps of,
    a) milling plant material comprising between about 0.5% to about 100% admix of a transgenic plant expressing at least one starch-digesting enzyme;
    b) combining milled plant material with a liquid to form a mash in a commercial slurry tank; and
    c) hydrolyzing the starch in the mash to reach a viscosity of less than 3000 cP.

2. The method of claim 1, wherein the admix comprises between about 8% to about 50% of a transgenic plant expressing at least one starch-digesting enzyme.

3. The method of claim 1, wherein the liquid is selected from the group consisting of water, backset, and stillage.

4. The method of claim 1, wherein the transgenic plant expressing a starch-digesting enzyme is expressing an alpha-amylase.

5. The method of claim 1, wherein the hydrolysis of the starch in the mash is performed at a pH from about pH 3.8 to about pH 5.0.

6. The method of claim 1, wherein the percentage of solids in the mash is selected from the group consisting of about 35% to about 60% milled plant material, about 35% to about 50% milled plant material, about 36% to about 40% milled plant material; about 37% to about 40% milled plant material; and about 40% to about 45% milled plant material.

7. The method of claim 1, wherein the percentage of solids in the mash is selected from the group consisting of at least about 35%, at least about 37%, at least about 39%, at least about 41%, at least about 43%, at least about 45%, at least about 49%, at least about 51%, at least about 53%, at least about 55%, at least about 57%, and at least about 60% milled plant material.

8. The method of claim 1, wherein the temperature of the mash does not exceed about 90 degrees C.

9. The method of claim 1, wherein the hydrolysis of the starch in the mash is performed in about 30 minutes to about 140 minutes.

10. The method of claim 1, wherein the hydrolysis of the starch in the mash is performed at about room temperature.

11. The method of claim 4, wherein the transgenic starch containing material is corn grain.

12. A method of reducing dough ball formation comprising the steps of,
    a) milling plant material comprising between about 0.5% to about 100% admix of a transgenic plant material expressing at least one starch-digesting enzyme;
    b) combining milled plant material with a liquid to form a mash in a slurry tank wherein the milled plant material does not form dough balls that can be detected in the effluent from the slurry tank.

13. The method of claim 12, wherein the admix comprises from about 8% to about 50% of a transgenic plant material expressing at least one starch-digesting enzyme.

14. The method of claim 12, wherein the liquid is selected from the group consisting of water, backset, and stillage.

15. The method of claim 12, wherein the transgenic plant material expressing at least one starch-digesting enzyme is expressing an alpha-amylase.

16. The method of claim 12, wherein the temperature of the mash does not exceed about 90 degrees C.

17. The method of claim 15, wherein the transgenic starch containing material is corn grain.

18. A method of reducing the viscosity of a mash comprising the steps of,
    a) milling plant material comprising between about 0.5% to about 100% admix of a transgenic plant material expressing at least one starch-digesting enzyme;
    b) combining milled plant material with a liquid to form a mash in a commercial slurry tank;
    c) hydrolyzing the starch in the mash;
    d) cooling the slurry to about ambient temperature wherein the viscosity of the cooled mash is less than about 2000 cP at about ambient temperature.

19. The method of claim 18, wherein the admix comprises from about 8% to about 50% of a transgenic plant material expressing a starch-digesting enzyme.

20. The method of claim 18, wherein the liquid is selected from the group consisting of water, backset, and stillage.

21. The method of claim 18, wherein the transgenic plant expressing at least one starch-digesting enzyme is expressing an alpha-amylase.

22. The method of claim 18, wherein the hydrolysis of the starch in the mash is performed at a pH from about pH 3.8 to about pH 5.0.

23. The method of claim 18, wherein the percentage of solids in the mash is selected from the group consisting of about 35% to about 60% milled plant material, about 35% to about 50% milled plant material, about 36% to about 40% milled plant material; about 37% to about 40% milled plant material; and about 40% to about 45% milled plant material.

24. The method of claim 18, wherein the percentage of solids in the mash is selected from the group consisting of at least about 35%, at least about 37%, at least about 39%, at least about 41%, at least about 43%, at least about 45%, at least about 49%, at least about 51%, at least about 53%, at least about 55%, at least about 57%, and at least about 60% milled plant material.

25. The method of claim 18, wherein the temperature of the mash does not exceed about 90 degrees C.

26. The method of claim 18, wherein the hydrolysis of the starch in the mash is performed in about 30 minutes to about 140 minutes.

27. The method of claim 18, wherein the hydrolysis of the starch in the mash is performed at about room temperature.

28. The method of claim 21, wherein the transgenic starch containing material is corn grain.

29. A method of increasing total solids of a mash while maintaining a desired viscosity comprising the steps of:
   a) milling plant material comprising between about 0.5% to about 100% admix of a transgenic plant expressing at least one starch-digesting enzyme;
   b) combining milled plant material with a liquid to form a mash in a slurry tank, wherein the total solids of the mash consists of about 35% to about 60% milled plant material; and
   c) hydrolyzing the starch in the mash to reach a desired viscosity.

30. The method of claim 29, wherein the desired viscosity is less than 3000 cP.

31. The method of claim 29, wherein the transgenic plant expressing at least one starch-digesting enzyme is expressing an alpha-amylase.

32. The method of claim 29, wherein the temperature of the mash does not exceed about 90 degrees C.

33. The method of claim 29, wherein the transgenic starch containing material is corn grain.

* * * * *